United States Patent [19]

Nordquist et al.

[11] Patent Number: 4,801,751

[45] Date of Patent: Jan. 31, 1989

[54] PROCESS FOR THE DISPROPORTIONATION OF ALKYLATED AROMATIC PRIMARY AMINES

[75] Inventors: Andrew F. Nordquist, Whitehall; Ronald Pierantozzi, Orefield, both of Pa.

[73] Assignee: Air Products and Chemicals, Inc., Allentown, Pa.

[21] Appl. No.: 913,826

[22] Filed: Sep. 30, 1986

[51] Int. Cl.$^4$ .............................................. C07L 85/24
[52] U.S. Cl. ................................... 564/305; 564/409
[58] Field of Search .............................. 564/409, 305

[56] References Cited

U.S. PATENT DOCUMENTS

| | | | |
|---|---|---|---|
| 3,123,644 | 7/1959 | Olin | 260/578 |
| 4,317,931 | 3/1982 | Wollensak et al. | 564/409 |
| 4,331,557 | 5/1982 | Drake | 564/490 |
| 4,387,247 | 6/1983 | Ratcliffe et al. | 564/420 |
| 4,405,812 | 9/1983 | Dean et al. | 564/409 |

FOREIGN PATENT DOCUMENTS 810751   9/1956   United Kingdom .

OTHER PUBLICATIONS

Corapcioglu, M. O. et al., *Carbon*, vol. 25, No. 4, pp. 569–578 (1987).
Holliday, A. K. et al., *Comprehensive Inorganic Chemistry*, pub. Pergammon Press, oxford, pp. 1173–1237.
Kirk, R. E. et al. *Encyclopedia of Chemical Technology*, vol. 2, pp. 881–899.
*Basic Concepts of Adsorption on Activated Carbon*, Pittsburgh Activated Carbon.

*Primary Examiner*—Glennon H. Hollrah
*Assistant Examiner*—John A. Sopp
*Attorney, Agent, or Firm*—Keith D. Gourley; James C. Simmons; William F. Marsh

[57] ABSTRACT

Alkylated aromatic primary amines undergo disproportionation and transalkylation in the presence of a carbon-containing catalyst at a temperature between 200° C. and 500° C. The carbon-containing catalyst may have carbon as the only active component, or optionally, may also contain a Group VIIIA metal, such as platinum, palladium, nickel, cobalt or mixtures thereof.

20 Claims, No Drawings

PROCESS FOR THE DISPROPORTIONATION OF ALKYLATED AROMATIC PRIMARY AMINES

TECHNICAL FIELD

The present invention relates to disproportionation and transalkylation reactions of alkylated aromatic primary amines.

BACKGROUND OF THE INVENTION

Meta-phenylenediamine, a useful chemical intermediate, has been prepared by the catalytic reduction of m-dinitrobenzene. Dinitration of benzene is difficult because the ring is deactivated and product separation is difficult, thus rendering the dinitrobenzene feedstock for m-phenylenediamine (M-PDA) synthesis very expensive. U.S. Pat. No. 4,387,247 discloses the reduction of di- or polynitro aromatic compounds by gaseous $H_2S$ over a solid catalyst. CO gas is added to promote formation of amino groups from all nitro groups in the molecule. The disproportionation of toluenediamine (TDA) to m-PDA was reported as a secondary reaction under the $CO/H_2S$ atmosphere.

U.S. Pat. No. 4,405,812 discloses a process for the ortho dealkylation of aromatic amines by contacting o-methyl substituted aromatic amines with a nickel catalyst at about 200°–400° C. The demethylation of dimethylanilines over nickel catalysts resulted in poor selectivity to the dealkylation product, toluidine when run under conditions similar to those used in aromatic hydrocarbon disproportionation.

U.S. Pat. No. 3,123,644 discloses a process for dealkylating a nuclear polyalkyl primary aromatic amine having a tertiary alkyl group of 4 or 5 carbon atoms on at least one ring carbon atom in the ortho-position with respect to the amino group. The polyalkyl primary aromatic amine is converted into a mono-nuclear primary aromatic amine by heating at a temperature in the range of 150°–350° C. under superatmospheric pressure with an acceptor aromatic amine and in the presence of a finely divided silica-alumina type catalyst.

U.K. patent application No. 810,751 discloses a process for the dealkylation of aromatic hydrocarbons. The process is carried out at a temperature from 450° to 700° C. and $H_2$ pressure above 40 atmospheres in the presence of a catalyst comprising active carbon by itself or with a small amount of metallic activator.

BRIEF SUMMARY OF THE INVENTION

The present invention is a process for the disproportionation of alkylated aromatic primary amines by contacting said alkylated aromatic amines with a carbon-containing catalyst at a temperature between 200° C. and 500° C. Additionally, the carbon-containing catalyst may also contain a Group VIIIA metal such as platinum, palladium, nickel, cobalt and mixtures thereof. The same catalysts and reaction conditions can be used for the transalkylation of two or more primary aromatic amines. Both the disproportionation and transalkylation reactions are useful methods of synthesizing m-phenylenediamine.

The process may be carried out in the liquid phase at autogenous pressure. Preferably the process is carried out under an inert atmosphere.

The present process is capable of selectively producing desired disproportionation products while limiting secondary product formation, e.g. formation of deaminated and/or coupled products. For example, catalysts with high hydrogenation activity and acidic supports, such as $Ni/Al_2O_3$, show high disproportionation activity but poor selectivity due to deamination and to reduction of aromatic rings. Additionally, the present process uses a preferred feedstock compared to processes involving the dinitration of benzene.

DETAILED DESCRIPTION OF THE INVENTION

The present invention is a process for the disproportionation of alkylated aromatic primary amines. An alkylated aromatic primary amine is contacted with a carbon-containing catalyst at a temperature between 200° C. and 500° C. The carbon-containing catalyst may have carbon as the only active constituent, such as activated carbon or unmodified graphites, or alternatively, may also contain between 0.01%–10% by wt. of a Group VIIIA metal such as platinum, palladium, nickel, cobalt and mixtures thereof. Examples of the latter include 5% platinum on carbon, 5% palladium on carbon, 5% nickel on carbon, Pt intercalated graphite, Pd intercalated graphite, Co intercalated graphite, carbons impregnated with up to 10% of a Group VIIIA metal reduced in $H_2$ prior to use, etc. While the above catalysts may be obtained from a variety of sources, the activated carbon may conveniently be produced from the pyrolysis of coal, vegetables, wood, coconut, or oil. Alternatively, the activated carbon may be produced by the pyrolysis of a carbon-containing substrate, for instance a hydrocarbon on an oxide support such as alumina.

The reaction is preferably carried out at a temperature between 300° C. and 400° C. with a range of 200° C. to 500° C. being acceptable. At lower temperatures the reaction rate is too slow to be practical and at higher temperatures deamination and coupled product formation occur. Reaction time will vary with the selected process conditions, with a preferred reaction time being that which is sufficient to give between 20% to 35% conversion. At lower conversions, product isolation costs are increased and at higher conversions, formation of secondary products occurs.

The reaction can be carried out via a variety of operating modes such as in a batch slurry reactor, e.g., a sealed stirred autoclave, at autogenous pressure, or by use of a CSTR or a trickle bed system with or without diluent gases. Other process steps can be taken to improve the reaction, such as recycling of heavy products through a flow reactor to reduce the rate of their formation, or separating products from the batch reactor by continuous distillation. Preferably the reaction is carried out under an inert atmosphere or a slight partial pressure of $H_2$ (10–200 psi). Under hhigh $H_2$ pressures (200–300 psi), or in the presence of steam, higher yields of heavy products are produced. Suitable reaction atmospheres include: low pressures of $H_2$ (e.g., about 10 psi); CO; ppm levels of $H_2S$ in an inert atmosphere; and ppm levels of $H_2S$ in a $H_2$ atmosphere.

Any suitable alkylated aromatic primary amine can be used as a reactant for the disproportionation reaction, example including: 2,4Toluenediamine (TDA); 2,6 TDA; 2,3 TDA; 3,4 TDA; o-, m-, p-toluidines; alkyl substituted anilines, alkyl substituted aromatic diamines, toluidines, etc. Representative disproportionation reactions using the above reactants include;

2,4 TDA→m-phenylenediamine+xylenediamine (XDA)

2,6 TDA→m-phenylenediamine+xylenediamine
Mixtures of 2,4 and 2,6 TDA→m-phenylenediamine+xylenediamine
p-toluidine→aniline+xylidine.

The choice of reactants will depend upon the desired product. Since m-phenylenediamine (m-PDA) is a high valued chemical intermediate for a variety of applications, reactants such as 2,4 TDA or 2,6 TDA which disproportionate to yield m-PDA are often the preferred reactants. Optionally, the primary amines employed in the reaction can be formed in situ from secondary or tertiary amines used as the starting material.

In addition to disproportionation reactions, the catalysts and process conditions of the present invention are also suitable for transalkylation reactions. Transalkylation results when an alkylated aromatic primary amine is reacted with a second aromatic compound. Transalkylation proceeds by the same mechanism and under the same conditions as the disproportionation described above, with the only difference being that the alkyl groups are transferred between aromatic compounds having different structures. Representative examples of such transalkylation reactions include:

TDA+aniline→m-PDA+toluidine
XDA+aniline→TDA+toluidine
XDA+cumene→benzene+isopropyl XDA It is believed that aromatic amine disproportionation and/or transalkylation occurs either by an acid catalyzed or a free radical mechanism, and the reaction will also occur slowly in the absence of catalyst due to thermal homolytic cleavage and radical formation. Activated carbons are known to contain high concentrations of unpaired electrons and are catalytic for disproportionation probably because they can abstract hydrogen from TDA, forming the benzyl radicals which are intermediates in disproportionation by a radical mechanism. Further, the activated carbons are unable to hold the hydrogen in a labile enough state to cause clevage of the bonds of the intermediates to enable product formation. The ability of the catalyst to activate hydrogen is still low enough that $H_2$ in the headspace is not activated for ring hydrogenation. As a result, hydrogenated rings, which are intermediates in the formation of heavy products, are not formed, and also hydrodeamination does not occur. Another possible explanation for the catalytic behavior of carbons may lie in their weak acidity. Carbons contain oxygenated functions which may be strong enough acids to catalyze disproportionation of TDA, but weak enough that heavy products are not formed.

Catalysts with high hydrogenation activity and acidic supports, such as $Ni/Al_2O_3$ have previously shown high disproportionation activity, but poor selectivity due to deamination and to the reduction of rings. These problems are avoided with carbon-containing catalysts of the present invention. In the prior art when TDA was selectively disproportionated over $Ni/Al_2O_3$, this was under a $CO/H_2S$ atmosphere and the disproportionation was probably selective because the atmosphere poisoned the ring hydrogenation activity of the Ni. Such an atmosphere is not necessary with the carbon catalysts.

Several examples were carried out in accordance with the process of the present invention. These examples are described below and are only meant to illustrate the invention and are not meant to be limiting.

EXAMPLE 1

A 300 cc stirred autoclave was charged with 50 g of 2,4 toluenediamine and 2.00 g NUCHAR® C-190N activated charcoal available commercially from Westvaco. The reactor was purged with He, sealed under 1 atmosphere He, heated to 350° C. over approximately 20 minutes, stirred at 700 RPM, and maintained at 350° C. for 4 h. The reactor was cooled to 80° C., a sample dissolved in methanol, the catalyst separated by sedimentation and the methanol soluble product analyzed for aromatic compounds by gas chromatography, using an internal standard to obtain a mass balance.

The composition of the product is given in Table 1 below. Conversion of TDA was 25.9% with 47.9% selectivity to m-phenylenediamine, which is 95.8% selectivity for disproportionation.

Selectivities (SEL) are calculated as follows:

$$\text{SELECTIVITY} = \frac{\text{moles of product } i}{\text{moles of } TDA \text{ converted}} \times 100\%$$

SELECTIVITY for Disproportionation =

$$SEL \text{ to m-PDA} + SEL \text{ to } XDA$$

HEAVIES = compounds containing two or more aromatic rings.

EXAMPLE 2

An identical test to Example 1 above was carried out for 16 h. Conversion of TDA was 41.7% with 45.8% selectivity to m-phenylenediamine and a disproportionation is selectivity of 87.8%. The product selectivity is set out in Table 1 below.

EXAMPLE 3

The procedure set out in Example 1 above was carried out using 2,6 TDA as the reactant. Conversion of TDA was 25% with 33.9% selectivity to m-phenylenediamine and a disproportionation selectivity of 59.6%. The product selectivity is set out in Table 1.

EXAMPLE 4

This example demonstrates the utility of the present invention for a commercial mixture of 2,4 TDA and 2,6 TDA (80:20 mixture). An autoclave, charged with 40.0 g of 2,4 TDA, 10.0 g of 2,6 TDA and 2.00 g of NUCHAR® carbon, was set up, operated and sampled at 4 h as in Example 1. The product selectivity is given in Table 1.

EXAMPLE 5

A catalyst was prepared by the following procedure:
A solution of 4.45 g of $Ni(CH_3COO)_2 \cdot 4H_2O$ in 100 ml anhydrous methanol was added to 20.0 g NUCHAR® C-190N carbon with constant stirring, after which the methanol was evaporated over a steam bath while stirring. The product was reduced at 400° C. under 1 atm $H_2$ for 20 h in a flow reactor, then transferred in air to the slurry reactor.

The catalyst was tested by the procedure described in Example 2 using 2.0 g of catalyst and 50 g of 2,4 TDA. Product selectvity is shown in Table 1.

EXAMPLE 6

The procedure of Example 2 above was carried out using 2.0 g of Engelhardt 5.0% Pt on carbon (Engelhardt lot 26505) as the catalyst, and 50 g of 2,4 TDA as the reactant. The product selectivity is given in Table 1.

EXAMPLE 7

Example 6 was repeated, with Engelhardt 5.0% Pd on carbon (Engelhardt lot 26885) employed as the catalyst in place of 5.0% Pt on carbon. The product selectivity of this run is also shown in Table 1 below.

TABLE 1

Catalyst Performance Data for the Disproportionation of TDA

| Example | Catalyst | TDA Conv | m-phenylene-diamine | Diamino-xylene | Toluidine | Xylidine | Diamino-mesitylene | Heavies | Disproportionation Selectivity |
|---|---|---|---|---|---|---|---|---|---|
| 1 | Nuchar | 25.9 | 47.9 | 47.9 | 0 | 0 | 0.66 | 3.51 | 95.8 |
| 2 | Nuchar | 41.7 | 45.8 | 42.0 | 0.11 | 0.08 | 1.17 | 10.80 | 87.8 |
| 3 | Nuchar | 25.0 | 33.9 | 25.7 | 0.28 | 0.21 | 1.07 | 38.9 | 59.6 |
| 4 | Nuchar | 38.2 | 31.5 | 29.2 | 0 | 0 | 0.75 | 38.5 | 60.7 |
| 5 | Ni/C | 48.7 | 34.7 | 33.0 | 0 | 0 | 0.86 | 31.5 | 67.7 |
| 6 | Pt/C | 57.2 | 35.7 | 34.8 | 0.2 | 0 | 1.28 | 22.3 | 70.5 |
| 7 | Pd/C | 49.4 | 43.0 | 42.4 | 0.3 | 0 | 1.59 | 12.7 | 85.4 |

EXAMPLE 8

While Examples 1-7 above all use diamines as the reactant, the present process can also be carried out using primary alkylated aromatic monoamines. To demonstrate this, the procedure detailed in Example 1 above was carried out using 50 g p-toluidine as starting material instead of 2,4-TDA. Product analysis by gas chromatography is given in Table 2 below.

TABLE 2

Disproportionation of p-toluidine using Carbon Catalyst Example 8

| Conv | m-toluidine | Aniline | Xylidine | Heavies |
|---|---|---|---|---|
| 12.8 | 8.8 | 34.5 | 30.7 | 26.0 |

EXAMPLE 9

Six runs were carried out using the process conditions and procedures of Example 1 for the disproportionation of TDA. Runs 1-5 employed the carbon-containing catalysts of the present invention, and Run 6 was a comparative run using Ni/Al$_2$O$_3$ catalyst which was employed in the reactions of U.S. Pat. No. 4,405,812. The Pt/C catalyst of run 2 was reduced with hydrogen prior to the reaction.

The results of all six runs as reported in Table 3 below.

TABLE 3

Catalyst Performance Data for the Disproportionation of TDA

| Run | Catalyst | Conv. | M-PDA | XDA | Tol. | Heavies |
|---|---|---|---|---|---|---|
| 1 | Nuchar C | 42 | 45 | 42 | 0 | 11 |
| 2 | Pt/C[1] | 44 | 49 | 46 | 0 | 3 |
| 3 | Pt/C | 57 | 35 | 34 | 0 | 22 |
| 4 | Ni/C | 49 | 35 | 33 | 0 | 31 |
| 5 | Pd/C | 49 | 43 | 42 | 0 | 13 |
| 6 | Ni/Al$_2$O$_3$ | 74 | 22 | 12 | 15 | 40 |

[1]Pre-reduced in H$_2$, Tol. = toluidine, m-PDA = metaphenylenediamine, XDA = xylenediamine The results shown in Table 3 above indicate that the prior art Ni/Al$_2$O$_3$ catalyst results in products that are formed by the polymerization of TDA or the products as well as the deamination product, toluidine. Consequently, although high conversions are achieved with the Ni/Al$_2$O$_3$ catalyst, it is not suitable for the present invention. The carbon-based catalysts of the present invention are thermodynamically limited to a lower conversion, but produce significantly less unwanted high molecular weight products, and are therefore well suited for the production of m-PDA and similar products.

Additionally, as can be seen by comparing runs 2 and 3, treating the Pt/C catalyst with H$_2$ prior to reaction with the TDA results in significant selectivity improvements.

Having thus described the present invention, what is now deemed appropriate for Letter Patent is set out in the following appended claims.

What is claimed is:

1. A process for the disproportionation of alkylated aromatic primary amines which comprises contacting said alkylated aromatic primary amines with a catalyst consisting essentially of activated carbon or unmodified graphite at a temperature between 200° C. and 500° C.

2. The process in accordance with claim 1 wherein said alkylated aromatic primary amine is a diamine.

3. The process in accordance with claim 2 wherein said disproportionation produces m-phenylenediamine.

4. The process in accordance with claim 3 wherein said disproportionation also produces xylenediamine.

5. The process in accordance with claim 4 wherein said alkylated aromatic primary amine is toluenediamine.

6. The process in accordance with claim 1 wherein said alkylated aromatic primary amines is contacted with said catalyst at a temperature between 300° C. and 400° C.

7. The process in accordance with claim 1 wherein said disproportionation is carried out under autogenous pressure.

8. The process in accordance with claim 1 wherein said disproportionation is carried in the presence of an inert blanket gas.

9. The process in accordance with claim 1 wherein said alkylated aromatic primary amine is toluidine.

10. The process in accordance with claim 9 wherein said disproportionation produces aniline and xylidine.

11. The process in accordance with claim 1 wherein said disproportionation is carried out in a batch slurry reactor in the liquid phase.

12. The process in accordance with claim 1 wherein said disproportionation is carried out in a continuous flow reactor.

13. The process in accordance with claim 1 wherein said catalyst is an activated carbon produced from the pyrolysis of coal, vegetables, wood, coconut, or oil.

14. The process in accordance with claim 1 wherein said catalyst is treated with $H_2$ prior to being contacted with the reactants.

15. The process in accordance with claim 1 wherein the selectivity for disproportionation products is greater than 95%.

16. A process for the transalkylation of two or more primary aromatic amines, wherein at least one aromatic amine is an alkylated aromatic amine, said process comprising contacting said primary aromatic amine with a catalyst consisting essentially of activated carbon or unmodified graphite at a temperature between 200° C. and 500° C.

17. The process in accordance with claim 16 wherein one of the primary aromatic amines is selected from the group consisting of: toluenediamine, xylenediamine and aniline.

18. The process in accordance with claim 16 wherein said transalkylation results in the production of m-phenylenediamine.

19. The process in accordance with claim 16 wherein said transalkylation is carried out at a temperature between 300° C. and 400° C.

20. The process in accordance with claim 16 wherein said catalyst is treated with $H_2$ prior to being contacted with the reactants.

* * * * *